United States Patent
Lee et al.

(10) Patent No.: US 7,019,133 B2
(45) Date of Patent: Mar. 28, 2006

(54) PROCESS FOR MAKING MYCOPHENOLATE MOFETIL BY TRANSESTERIFICATION

(75) Inventors: Kwang-Chung Lee, Taoyuan (TW); Shu-Chuan Lin, Su-Lin (TW); Ray-Hwa Chiu, Su-Lin (TW)

(73) Assignee: Chunghwa Chemical Synthesis & Biotech Co., Ltd., Taipei Hsien (TW)

( * ) Notice: Subject to any disclaimer, the term of this patent is extended or adjusted under 35 U.S.C. 154(b) by 134 days.

(21) Appl. No.: 10/750,466

(22) Filed: Dec. 29, 2003

(65) Prior Publication Data

US 2004/0167130 A1   Aug. 26, 2004

(30) Foreign Application Priority Data

Feb. 21, 2003   (TW) ................... 92103728

(51) Int. Cl.
*C07D 413/02* (2006.01)

(52) U.S. Cl. .................................... 544/153
(58) Field of Classification Search ........... 544/153, 544/170
See application file for complete search history.

(56) References Cited

U.S. PATENT DOCUMENTS

| 4,753,935 A | * | 6/1988 | Nelson et al. | ........... 514/233.5 |
| 5,247,083 A | * | 9/1993 | Knox et al. | ................. 544/153 |
| 5,380,879 A | * | 1/1995 | Sjogren | ...................... 549/310 |

FOREIGN PATENT DOCUMENTS

| WO | WO 00/34503 | * | 6/2000 | ................. 544/153 |
| WO | WO03042393 A1 | * | 5/2003 | |

OTHER PUBLICATIONS

Jerry March, Advanced Organic Chemistry, 1985, 3$^{rd}$ Ed., pp. 348-353.*

* cited by examiner

*Primary Examiner*—Joseph K. McKane
*Assistant Examiner*—Nyeemah Grazier

(57) ABSTRACT

A process for making mycophenolate mofetil comprising: conducting a catalytic transesterification by reacting a low-carbon alkyl ester of mycophenolic acid with 2-morpholinoethanol [also named as 4-(2-hydroxyethyl) morpholine] to obtain a crude product of mycophenolate mofetil, which is then isolated and purified.

4 Claims, No Drawings

PROCESS FOR MAKING MYCOPHENOLATE MOFETIL BY TRANSESTERIFICATION

BACKGROUND OF THE INVENTION

U.S. Pat. No. 5,247,083 to Martin Knox et al. disclosed a process for making mycophenolate mofetil by refluxing mycophenolic acid with 2-morpholinoethanol in an inert organic solvent even without the use of catalyst. However, the reaction requires a long time period. For example, when the reaction completion was 94.9% by refluxing the reaction mixture at 125~129° C., it already consumed 63 hours. The long reaction time may increase the production cost and may also waste energy when heating the reaction mixture for such a long time period.

The present inventor has found the drawbacks of the conventional process and invented the present process for making mycophenolate mofetil by shortening the reaction time in order to reduce the production cost and improve the product purity.

SUMMARY OF THE INVENTION

The object of the present invention is to provide a process for making mycophenolate mofetil comprising: conducting a catalytic transesterification by reacting a low-carbon alkyl ester of mycophenolic acid with 2-morpholinoethanol [also named as 4-(2-hydroxyethyl) morpholine] to obtain a crude product of mycophenolate mofetil, which is then isolated and purified.

DETAILED DESCRIPTION

For a direct esterification of mycophenolic acid with 2-morpholinoethanol [or named as 4-(2-hydroxyethyl) morpholine], the reaction is difficult and may take a longer reaction time period.

One way may be considered is to first activate the mycophenolic acid (MPA) to be an acyl chloride or acid anhydride of the MPA, and then reacted with 2-morpholinoethanol to produce mycophenolate mofetil (such as taught by U.S. Pat. No. 4,753,935). However, the activity may be too strong, thereby accompanying with unexpected side reactions and seriously causing impurities of the product.

Accordingly, the mycophenolic acid may be first esterified, and then reacted with the 2-morpholinoethanol to obtain the mycophenolate mofetil in accordance with the present invention.

This invention discloses a process by preliminarily conducting an esterification of the mycophenolic acid with an alkyl alcohol of low carbon alkyl group ($C_1$~$C_4$) to form a low-carbon alkyl ester, which is then reacted with the 2-morpholinoethanol to obtain the mycophenolate mofetil.

The mycophenolate mofetil (1) of the present invention is obtained by the transesterification of the alkyl mycophenolate (2) with 2-morpholinoethanol (3) in the presence of a catalyst as shown in the following reaction formula:

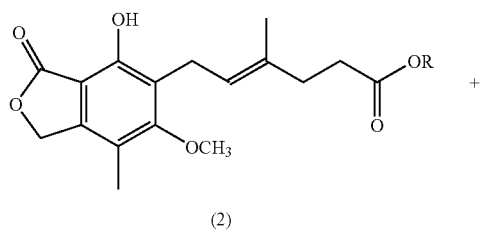

(2)

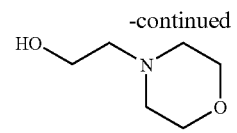

(3)

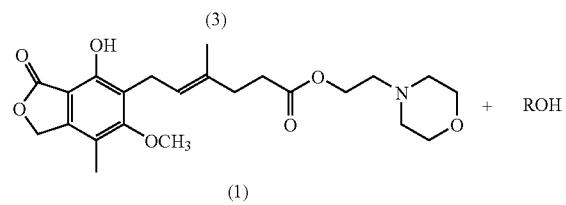

(1)

wherein R is an alkyl group selected from the group consisting of methyl, ethyl, propyl and butyl.

After the completion of transesterification, the reaction liquid is added therein with aqueous solution of sodium bicarbonate and ethyl acetate to form a water layer and an organic layer. An aqueous solution of acid such as hydrochloric acid is added into the organic layer to obtain a hydrochloric acid salt of mycophenolate mofetil which is soluble in water; while the unreacted alkyl mycophenolate (2) is not formed as a hydrochloric acid salt (HCl salt) and is soluble in organic solvent to thereby be easily separated from the HCl salt of mycophenolate mofetil by using an organic solvent to extract and remove the unreacted methyl mycophenolate. Then, an aqueous solution of base such as sodium hydroxide is provided to neutralize the hydrochloric acid to recover the mycophenolate mofetil which is then extracted by an organic solvent.

The catalyst as used in this esterification may be selected from the group consisting of: alkaline metal salt, alkaline earth metal salt, tin oxides and stannous oxides, and may preferably be dibutyl tin oxide, having a catalyst content of 1~200 (weight) %, preferably 5~70 (weight) %, based on the weight of alkyl mycophenolate.

The quantity of 2-morpholinoethanol as used in the transesterificaton may range in 1~20 equivalents, preferably being 1.01~2 equivalents. The esterification reaction temperature is 30~180° C., and preferably being 80~160° C. The organic solvent as used in the reaction may be selected from the group consisting of: benzene, toluene, xylene and the mixture thereof. The reaction may also preclude the use of any organic solvent. The organic solvent used for extraction in this invention may be selected from: benzene, toluene, xylene, ethyl acetate, dichloro-methane, and the mixture thereof; or any other water-insoluble organic solvent.

The present inventions may be further described in detail with reference to the following example, which is given for description, not to limit the scope of the present invention.

The alkyl mycophenolate may be obtained by reacting the MPA with an alkyl alcohol in the presence of a catalyst overnight (less than 24 hours) to be the alkyl mycophenolate, such as methyl mycophenolate as shown in Example 1.

EXAMPLE 1

In a reactor, 20.0 grams (59.8 milli moles) methyl mycophenolate, 8.2 g (62.6 milli moles) 2-morpholinoethanol, 40 ml toluene and 7.4 g (29.8 milli moles) dibutyl tin oxide were added. The reaction mixture (liquid) was heated until an internal temperature 120° C. was reached and the temperature (120° C.) was maintained for performing the transesterification reaction for 24 hours.

As checked by HPLC at this moment, there was 1.3% methyl mycophenolate still unreacted. The reaction mixture was cooled to room temperature, added with 100 ml aqueous solution of saturated sodium bicarbonate and 100 ml ethyl acetate, and further agitated for 5 minutes. The insoluble matters were filtered off by celite. A separating funnel was provided for separating the aqueous layer and the organic layer. The aqueous layer was extracted with an organic solvent, i.e., 100 ml ethyl acetate.

The organic layer combined with the organic solvent, which may contain the mycophenolate mofetil and the unreacted reactants, was added therein with 200 ml water, and further acidified to be an acidic solution by adding 6N hydrochloric acid to obtain a pH value of 1.5. The mycophenolate mofetil was formed as a hydrochloric acid salt to therefore be soluble in the water of the acidic solution while the methyl mycophenolate was not formed as a hydrochloric acid salt, thereby being insoluble is the water. Again, an aqueous layer (containing acid salt of mycophenclate mofetil) layer and an organic layer was thus formed. The aqueous layer was extracted with ethyl acetate (100 ml for each extraction) twice to remove the unreacted methyl mycophenolate.

The aqueous layer containing the hydrochloric acid salt of mycophenolate mofetil was now added therein with 20% sodium hydroxide aqueous solution to be basic (pH=7.7) to neutralize the hydrochloric acid and recover the mycophenolate mofetil in the aqueous solution.

Ethyl acetate was provided to twice extract the mycophenolate mofetil from the aqueous solution, each extraction using 100 ml of ethyl acetate. The extracts of ethyl acetate were combined as an organic layer and washed with 100 ml aqueous solution of saturated sodium bicarbonate.

The organic layer was purified as being dried by anhydrous magnesium sulfate, filtered, and evaporated under reduced pressure to obtain 23.2 grams of mycophenolate mofetil, with high purity of 99.9% and high yield of 89.5%.

From the above-mentioned example, it is understood that the present invention may produce mycophenolate mofetil with high purity and high yield in a short reaction time period to thereby reduce the production cost and prevent from wasting of energy to be superior to the prior arts.

I claim:

1. A process for making mycophenolate mofetil comprising the steps of:
   A. conducting a transesterification by reacting an alkyl mycophenolate with 2-morpholinoethanol in the presence of an organic solvent and a catalyst selected from the group consisting of alkaline metal salt, alkaline earth metal salt, tin oxide and stannous oxide to produce crude mycophenolate mofetil;
   B. adding an acid aqueous solution into said crude mycophenolate mofetil to form an acid salt of mycophenolate mofetil to be soluble in the acid aqueous solution to be separated from the unreacted reactants insoluble in the acid aqueous solution;
   C. basifying the acid aqueous solution to be a base aqueous solution by adding a base therein; and
   D. extracting the mycophenolate mofetil from the base aqueous solution by an extracting organic solvent, and purifying the mycophenolate mofetil.

2. A process according to claim 1, wherein said alkyl mycophenolate is selected from the group consisting of: methyl mycophenolate, ethyl mycophenolate, propyl mycophenolate and butyl mycophenolate.

3. A process according to claim 1, wherein said catalyst is dibutyltin oxide.

4. A process according to claim 1, wherein said extracting organic solvent is selected from the group consisting of: benzene, toluene, xylene, ethyl acetate, dichloro methane, and the mixture thereof.

* * * * *